(12) United States Patent
Altenschöpfer et al.

(10) Patent No.: US 7,608,282 B2
(45) Date of Patent: Oct. 27, 2009

(54) TRANSDERMAL GRANISETRON

(75) Inventors: Peter Altenschöpfer, Ortenburg (DE); Adam Charles Watkinson, Victoria (AU)

(73) Assignee: Strakan International Limited, Hamilton (BM)

( * ) Notice: Subject to any disclaimer, the term of this patent is extended or adjusted under 35 U.S.C. 154(b) by 260 days.

(21) Appl. No.: 10/544,259

(22) PCT Filed: Feb. 5, 2004

(86) PCT No.: PCT/GB2004/000403

§ 371 (c)(1), (2), (4) Date: Dec. 9, 2005

(87) PCT Pub. No.: WO2004/069141

PCT Pub. Date: Aug. 19, 2004

(65) Prior Publication Data

US 2006/0177493 A1 Aug. 10, 2006

(30) Foreign Application Priority Data

Feb. 5, 2003 (GB) ................. 0302662.2

(51) Int. Cl.
*A61F 13/00* (2006.01)
*A61L 15/00* (2006.01)
*A61L 15/16* (2006.01)

(52) U.S. Cl. .............. 424/443; 424/445; 424/446; 424/447; 424/449

(58) Field of Classification Search .................. None
See application file for complete search history.

(56) References Cited

U.S. PATENT DOCUMENTS 3,269,994 A * 8/1966 Horn et al. ............. 428/355 AK
5,656,286 A * 8/1997 Miranda et al. ............. 424/449

FOREIGN PATENT DOCUMENTS

| CA | 2 341 998 | 9/2002 |
|---|---|---|
| EP | 1 163 902 A2 | 12/2001 |
| WO | WO 9401095 A2 * | 1/1994 |
| WO | WO 94/07468 | 4/1994 |
| WO | WO 98/53815 | 12/1998 |
| WO | WO 9853815 A1 * | 12/1998 |
| WO | WO 00/47208 | 8/2000 |
| WO | WO 0047208 A1 * | 8/2000 |
| WO | WO 01/74338 | 10/2001 |

OTHER PUBLICATIONS

Biswas and Rudra, Comparison of granisetron and granisetron plus dexamethasone for the prevention of postoperative nausea and vomiting after laparoscopic cholecystectomy. Acta Anaesthesiol Scand., 47:79-83, 2003.
Cupissol et al., Evaluation of the bioequivalence of tablet and capsule formulations of granisetron in patients undergoing cytotoxic chemotherapy for a malignant disease. J.Pharm.Sci., 82:1281-1284, 1993.
Friedman et al., Oral granisetron for the prevention of acute late onset nausea and vomiting in patients treated with moderately emetogenic chemotherapy. Oncologist, 5:136-143, 2000.
Gralla et al., Recommendations for the use of antiemetics: Evidence based, clinical practice guidelines. Journal of Clinical Oncology, 17:2971-2994, 1999.
Guillem et al., High efficacy of oral granisetron in the total control of cyclophosphamide-induced prolonged emesis. Proceedings of the American Society of Oncology, 17:46, 1998.
Kalaycio et al., Continuous-infusion granisetron compared to ondansetron for the prevention of nausea and vomiting after high-dose chemotherapy. J. Cancer Res. Clin. Oncol., 124:265-269, 1998.
Noble et al., a double-blind, randomized, crossover comparison of granisetron and ondansetron in 5-day fractionated chemotherapy: assessment of efficacy, safety and patient preference. Eur. J. of Cancer, 30: 1083-1088, 1994.
Physicians Desk Reference (2001) entry for Kytril®.
Porzio et al., Pruritus in a patient with advanced cancer successfully treated with continuous infusion of granisetron. Support Care Cancer, Jan. 21, 2004.

* cited by examiner

*Primary Examiner*—S. Tran
(74) *Attorney, Agent, or Firm*—Foley & Lardner LLP; Stephen E. Reiter (57) ABSTRACT

Adhesive patches for the transdermal administration of granisetron, comprise an acrylic adhesive containing non-acidic nucleophilic moieties which substantially increase flux of granisetron across the skin.

28 Claims, 3 Drawing Sheets

TRANSDERMAL GRANISETRON

The present invention relates to transdermal patches comprising granisetron, to uses therefor and to methods for their preparation.

Nausea and vomiting are frequently the most debilitating and discouraging symptoms of medications administered to cancer patients. The side effects of emesis are not just unpleasant because of the condition, per se, they can lead to serious dehydration and even malnutrition.

Patients on regimens of anti-cancer drugs that have high associated emetigenic potential (e.g. cisplatin, streptozotocin, carmustine, procarbazine, mechlorethamine and dactinomycin) are particularly affected and, therefore, particularly benefit from aggressive, concomitant administration of anti-emetic drugs to curb intractable nausea and vomiting. Other patient groups that benefit from such treatment regimens are those suffering from post-operative nausea and vomiting.

Cytotoxic chemotherapy is thought to release serotonin from certain cells of the small intestine. The released serotonin may stimulate the vagal afferent nerves through the 5-$HT_3$ (5-hydroxytryptamine$_3$) receptors, thus stimulating the vomiting reflex. Accordingly, it is assumed that 5-$HT_3$ receptor antagonistic drugs, such as ondansetron, granisetron and tropisetron, exert their effects by blocking serotonin, both peripherally, on vagal nerve terminals, and centrally, in the chemo-receptor trigger zone.

5-$HT_3$ receptor antagonistic antiemetics are currently administered intravenously, orally, or rectally. Intravenous administration can only be performed under medical supervision, and causes significant patient discomfort, such as redness and burning, at the injection site. Problems are compounded in paediatric medicine, owing to children's dislike of needles, and there are always concerns regarding needle-stick injuries. Oral administration has disadvantages associated with its frequency (up to four times daily), as well as the issues resulting from utilisation of such a route of delivery in a patient suffering severe nausea and vomiting and patients suffering from head and neck cancer can often not swallow properly. The pulsatile nature of oral delivery may also cause problems resulting from deviations from the therapeutic window (often responsible for side effects). Rectal delivery circumvents, to some extent only, the pulsatile nature of oral delivery and is not the most convenient, nor widely acceptable, approach to drug delivery.

Hence, there is a need for a non-oral drug delivery system capable of maintaining constant plasma levels of antiemetic agents over extended periods of time. Indeed, there are other indications for 5-$HT_3$ receptor antagonists that cannot currently be fully exploited, and that would benefit from more controlled delivery than that currently available.

The 5-$HT_3$ receptors are located primarily in peripheral and central neurons, and appear to be involved in the depolarisation of peripheral neurons, pain, and the emesis reflex. Thus, other indications include pruritus (Porzio, et al.), migraine, anxiety, and cognitive and psychotic disorders, and, more specifically, the treatment or prevention of depression, schizophrenia, psychosis in postnatal depression, fibromyalgic pain, irritable bowel syndrome, alcoholism, obstructive sleep disturbed breathing, motion sickness, loss of cognitive function, urinary incontinence, dyskinesia, systemic lupus erythematosus, drug-induced pruritus, chronic fatigue syndrome (CFS—The, et al., 2003), premature ejaculation, and eating disorders, such as bulimia.

Transdermal delivery of drugs through the skin is a recognised method for maintaining relatively steady plasma levels of therapeutic agents whilst also circumventing the pain, discomfort and inconvenience of intravenous, oral and rectal drug delivery. Hence, post-chemotherapy and post-operative transdermal anti-emetigenic therapy has the potential to ease the suffering of patients who are not only experiencing nausea and vomiting, resulting from their primary therapy, but also suffering significant discomfort associated with their medical condition per se.

Various attempts have been made to provide successful, transdermal administration of 5-$HT_3$ receptor antagonists. However, the majority of patent publications on the subject simply includes the option of transdermal delivery, as one option among many, as a possible route of administration.

Similarly, various patent publications relating to specific transdermal or iontophoretic devices cite ondansetron, amongst others, for possible inclusion in these devices. U.S. Pat. No. 5,372,819 (Minnesota Mining and Manufacturing Company) cites, amongst a large number of other compounds of numerous classes, metoclopramide and ondansetron as antiemetics for inclusion in a transdermal patch. However, there are no specific examples for any of the drugs cited that demonstrate the therapeutic potential of the device, nor which address the issues concerning the transdermal delivery of these compounds. Similarly, WO 94/07468 (Cygnus Inc.) cites granisetron and ondansetron as exemplary antiemetics in a less extensive list of compounds for inclusion in another transdermal device.

Japanese laid-open no. 8-34731 discloses percutaneous preparations of granisetron, using such formulation forms as creams, liniments, lotions, gels, tapes and patches. These formulations comprise a vehicle and a permeation enhancer, which may be selected from alcohols, fatty acids, esters of these, and others. The Examples of this publication use the skin of the hairless mouse to establish likely flux in humans. Despite the skin of these animals having about 10 fold greater permeability than human skin, it was still necessary to employ a 100 $cm^2$ patch. An object of the present invention is to reduce the size of patch necessary to achieve antiemetic blood plasma levels of drug.

Ondansetron is a widely used 5$HT_3$ antagonist. Owing to the systemic nature of the antiemetic effect, relatively high therapeutic plasma levels of ondansetron are required to achieve efficacy. Hence, the successful transdermal delivery of a therapeutically effective amount of ondansetron requires that the transdermal device provide a relatively high flux of the drug across the skin. Such high fluxes can only be maintained over a clinically relevant time period if the drug loading within the patch is great enough to ensure that drug depletion does not reduce delivery rate with time, i.e. a high flux is sustained.

High drug loading in transdermal patches is generally achieved by the use of so-called 'reservoir patches'. Reservoir patches contain solutions of drug that allow higher loadings than can normally be achieved in the alternative matrix patch technology. These high drug loadings are achieved by the use of relatively high volumes of solvents, such as ethanol or propylene glycol, which are often irritating to the skin. By virtue of the volume of their contents, reservoir patches are normally physically and visually bulky and, once applied, are not flush with the skin surface. Such attributes make them cosmetically unacceptable to many patients.

Furthermore, adherence of reservoir patches to the skin can be sub-optimal, as the adhesive is only positioned around the periphery of the patch, which is intended to allow the drug to permeate from the central reservoir across a rate controlling membrane in contact with the skin.

By way of contrast, matrix patches have the ability to adhere to the skin much more effectively, owing to the fact that the area of adhesive in contact with the skin is coterminous with the total, effective area of the patch, thereby also securing a maximal secure interface between patch and skin. This has implications for the effective utilisation of the skin as a route of drug delivery, as well as simply ensuring that the patch remains in place.

However, the very nature of a matrix patch sets a limit on the amount of active material that can be carried by the patch, as reservoir for the drug is provided by the adhesive matrix, rather than separately. Matrix patches simply are not suitable for drugs that need to be administered in high amounts, such as ondansetron, as they cannot carry sufficient drug. For example, WO 00/47208 (Sam Yang Corporation) and EP-A-1,064,939 (Novosis Pharma AG) disclose transdermal ondansetron reservoir patches, while WO 00/47208 specifically excludes matrix patches on the grounds that the obtainable drug loading is insufficient.

WO 01/74338 discloses a lerisetron pharmaceutical preparation in the form of a transdermal therapeutic system (TTS) comprising a backing layer, connected to it an at least single-layer pressure-sensitively adhesive, lerisetron active substance reservoir based on silicone pressure-sensitive adhesive (s), and a removable protective layer.

WO98/53815, to 3M, discloses compositions comprising tropisetron or granisetron in acrylic adhesives, and that are suitable for transdermal administration. However, adhesives containing nucleophilic, such as hydroxyl, moieties are taught against, as it is demonstrated that tropisetron is unstable in their presence. The authors speculate that this instability may be caused by increased cross-linking within the adhesive that may also involve binding of the drug to the polymer, and that the basic nature of the drugs may catalyse this process. Such reactions may involve the production of undesirable drug degradation products and any drug/polymer binding could be expected to reduce flux.

However, we have now found that, while adhesives comprising electronegative groups, such as COOH groups, cannot be used in the manufacture of effective transdermal patches, adhesives comprising hydroxyl groups are significantly better than non-nucleophilic, electroneutral adhesives, and that such adhesives substantially enhance flux of granisetron, for example.

Thus, in a first aspect, the present invention provides an adhesive patch suitable for the transdermal administration of granisetron, wherein the adhesive is an acrylic adhesive containing non-acidic hydroxyl moieties.

Patches of the present invention preferably have granisetron (N-endo-9-methyl-9-azabicyclo[3.3.1]non-3-yl-1-methylindazole-3-carboxamide hydrochloride) or ramosetron [(R)-5-[(1-methyl-3-indolyl)carbonyl]4,5,6,7-tetrahydro-1H-benzimidazole hydrochloride)], or a mixture thereof, as the active ingredient, although mixtures are less preferred. It will be appreciated that all references herein to granisetron include reference to ramosetron and mixtures thereof, unless otherwise specified, or apparent.

It is preferred that the non-acidic hydroxyl moieties, or OH groups as they are also referred to herein, are provided by the simple expedient of incorporating the appropriate monomers during manufacture of the adhesive polymer. Suitable monomers may include the acrylates and methacrylates substituted in any desired manner. Particularly preferred acrylates are the hydroxymethyl, hydroxyethyl and hydroxypropyl acrylates, especially hydroxyethylacrylate (HEA). Preferred methacrylates are the hydroxymethyl and hydroxyethyl methacrylates.

Hydroxyl groups of the adhesives of the present invention are preferably not associated with any other polar moiety, or part of any other group. In particular, it is preferred that the OH group not be part of any COOH, NCOH and the like groups. While minimal levels of such groups may be tolerated, it is preferred that adhesives of the present invention have substantially no detectable levels of such groups.

Adhesives of the present invention are preferably pressure sensitive. Acrylic pressure sensitive adhesives are generally made with a substantial amount of a primary acrylate monomer which, in most commercial acrylic adhesives, is limited to either 2-ethylhexyl acrylate or butyl acrylate. Other monomers may be suitable, provided that they have a sufficiently low glass transition temperature ($T_g$).

Modifying monomers are also commonly used, and may be selected from virtually any vinyl monomer. The modifying comonomers may be selected from those having a modifying effect on tack, such as vinyl acetate and styrene in polyacrylates, and vinyl pyrrolidone and acrylonitrile in polymethacrylates, to comonomers containing functional groups, which can include those mentioned above where it is desired to incorporate an OH group.

Typical levels of primary monomer are between 50 and 90% by weight, but up to 98%, and the modifying monomer, such as vinyl acetate, styrene or methacrylonitrile, is typically present in an amount of about 10 to 40% w/w. The functionality, or hydroxyl, comonomer is preferably present in an amount of from 0.5 to 20% w/w, preferably between 3 and 10% w/w by weight of total monomers. As the functionality monomer is increased, levels of the other constituents are reduced, pro rata. Additionally, the adhesive may contain cross-linking monomers such as glycidylmethacrylate at levels between 0.05 and 1% by weight, in place an equivalent amount of primary monomer.

The adhesive patches of the present invention are effective without having to incorporate any plasticisers or permeation enhancers, such as isopropyl myristate (IPM). This is advantageous, as it reduces the number of constituents, and excludes a possible source of irritation, as well as excluding a substance that reduce the cohesion of the adhesive. Permeation enhancers are generally required in transdermal patches. However, in the patches of the present invention, the presence of the polar residues has a surprising effect on the transdermal flux, increasing permeation to a level where substantially the whole load can be dispensed in a 24 hour period, if desired.

Indeed, any form of chemical interaction with the adhesive would normally be expected only to hamper flux and transdermal penetration by retarding release. In the accompanying Examples, we demonstrate that the presence of hydroxyl groups in the adhesive actually substantially facilitates release, compared with release from directly comparable adhesives with no polar groups. It is particularly surprising that initial release levels are several orders of magnitude higher than from non-nucleophilic adhesives, and enables transdermal patches made with an adhesive of the invention to be used in circumstances requiring effective levels of granisetron within a matter of hours.

The patches of the present invention also have the ability to dispense the granisetron in a substantially uneven form, but in a manner ideal for the treatment of chemically induced emesis. Such emesis can be divided into acute and delayed, with the acute emesis resulting from the chemotherapy and high levels of anti-neoplastic drug, and the delayed form being a longer term response. The acute reaction necessitates higher levels of antiemetic over a period of about 12 hours from administration, while the delayed form needs a lower level over subsequent days. The patches of the present invention can be employed to provide this sort of regimen and, if used individually, will generally tend to provide such a regimen.

It will be appreciated that the term "patch" encompasses any adhesive construct suitable to adhere to and to dispense granisetron to the skin, and will generally comprise a backing layer with adhesive on one side, physiologically effective amounts of granisetron being loaded, or loadable, in the adhesive. The construct may be in the form of a flexible strip that may be cut into portions, for example.

In single dose chemotherapy, 5HT$_3$ antagonists are commonly used for the prevention of acute nausea and vomiting associated with the administration of emetogenic chemotherapy. Although the efficacy of these agents in the acute setting is clear, the most appropriate dose and the relationship between efficacy and plasma levels are not. Published studies also clearly demonstrate the efficacy of 5HT$_3$ antagonists (administered with dexamethasone) in delayed emesis (Guillem et al., 1998; Friedman et al., 2000) but again do not address issues of dose response.

Despite the lack of information regarding their therapeutic relevance, plasma profiles are still a useful marker in demonstrating bioequivalence when switching dosage form. Most dosage forms (injections, tablets and oral syrups) of the 5HT3 antagonists result in plasma profiles typical of pulsatile drug delivery i.e. short $T_{max}$ values and relatively high $C_{max}$ values followed by decreases in plasma levels concomitant with drug half life.

The most common granisetron regimen in chemotherapy is an initial dose of 1 or 2 mg prior to treatment for the prevention of acute emesis, followed by a 2 mg daily dose for 3 to 5 days in combination with dexamethasone, for the prevention of delayed emesis. Continual twice daily dosing of 1 mg in cancer patients (Physicians Desk Reference, 2001) yields average peak plasma levels of 6 ng/ml and a clearance value of 0.52 L/hr/kg. For a 60 kg patient these data indicate that a flux of about 190 μg/h from a transdermal patch would be sufficient to maintain plasma levels of 6 ng/ml. However, maintenance of plasma levels at these $C_{max}$ values is not required for efficacy in delayed emesis (Cupissol et al., 1993) and the minimum required therapeutic plasma level in acute emesis is not known.

The minimum therapeutic plasma level required for efficacious use of any drug is ideally assessed by titrated, prolonged IV infusion studies coupled to clinical response in patients. Continual IV infusion of granisetron at a rate of only 40 μg/h has been shown (Kalaycio et al., 1998) to alleviate delayed emesis in cancer patients, suggesting that maintenance of a lower plasma level (approximately 1.5 ng/ml) may be more appropriate in this respect.

The main limitation of a patch in this setting is the delay in achieving plasma levels appropriate for efficacy. Whilst $T_{max}$ values associated with oral granisetron are approximately 2 hours, those associated with its transdermal administration are generally longer. Levels associated with the patches of the present invention can already begin to show efficacy by about 2 hours, so that patches of the invention can be useful in the treatment of acute emesis.

In general, patches of the invention are preferably applied to the patient between 2 and 48 hours prior to treatment, with a period of between 6 and 24 hours being more preferred. Good results are seen when the patch is applied between 12 and 16 hours before treatment, for example.

In the context of nausea and vomiting, it will be appreciated that the patches of the invention are suitable for the treatment of any form of nausea and emesis associated with activation of 5-HT$_3$ receptors. Such conditions are generally associated with cancer therapy, including radiotherapy, multi-day therapy, fractionated therapy, and terminal cancer therapy, each of which is individually contemplated by the present invention. Other forms of cancer therapy are also contemplated by the invention, including those exemplified herein.

Where it is desired to provide a continuous high level of granisetron, then patches may be applied twice a day, for example, or as often as indicated by the skilled physician.

Levels of granisetron may be up to about 12%, preferably up to about 10% by weight although, in DuroTak 387-2287, an adhesive provided by National Starch, 8% w/w is generally higher than preferred, as crystallisation can occur. Thus, in preferred adhesives of the invention, levels of granisetron are below 8% w/w. It is preferred to provide levels of granisetron above 3%, preferably above 4%, and more preferably above 5% w/w. It is particularly preferred to provide levels between 6% and 7.7% w/w. In preferred adhesive, no crystallisation was observed in patches containing up to 7.7% after one month. The concentration of granisetron in the patch is between 6 and 8%, but is subject to such considerations as age and weight of the patient, as well as physical condition and other concomitant treatments or therapies, suitable levels of granisetron being readily determined by the skilled physician. A preferred level is currently 6% w/w.

It is generally preferred to avoid crystallisation of granisetron in the patches of the present invention, owing to cost considerations. However, crystallisation readily affords a reservoir of drug, which can dissolve into the patch, whence it can be dispensed to the patient, once the patch has been depleted, at least partially, of the initial levels of granisetron. Where a patch is intended for immediate rapid delivery, for example, then crystallisation provides no advantage, and adds to production costs.

It will also be appreciated that the size of the patch may be any that is suitable. In general, patches of up to about 100 cm$^2$, or greater, are suitable to deliver effective quantities of granisetron to the patient. If such a size is desired, then this may be achieved by the use of one patch, which may have any desired shape, such as round or square and which may be perforated, for example, or two or more patches may be used. It will also be appreciated that treatment may start with one or more patches to the total desired area, and that levels of granisetron may then be maintained by regular application of smaller patches at intervals readily determined by the skilled physician, for example.

In general, at a loading of about 6% w/w of granisetron, it has been found that a suitable size patch is between 10 and 100 cm$^2$, more preferably between 15 and 50 cm$^2$, with a patch of around 40 cm$^2$ generally providing the equivalent plasma levels of a tablet containing 1 mg granisetron. It will be appreciated that the patches may be provided in varying sizes, or may be cut to size, and that the size and loading are readily determined by the skilled physician and will largely determine the plasma levels desired.

It is also an advantage of the present invention that flux from the patch is so great that small patches are readily employed to substantial effect, and that large patches, such as those disclosed in WO98/53815, are not generally necessary, unless very large fluxes are required, for example.

Polar groups in the polymer chains of adhesives have the added benefit of increasing skin adhesion. The inclusion of such groups also increases formulation options as it allows cross-linking of the adhesives to be achieved if required, thereby improving cohesion of the adhesive matrix in terms of three dimensional stability.

It will be appreciated that patches of the present invention may comprise components other than adhesive and granisetron. Suitable backings, for example, are described hereinbelow. They may take any suitable form, and may be in the form of films or materials, for example. Films may be selected for breathability and/or their occlusive properties. It is possible to use metallised films, but it is generally preferred to use plastics, such as polyethylene terephthalate (PET). Materials may be selected from woven and non-woven, with non-wovens generally providing a greater degree of flexibility. Such materials are generally highly porous, and it is preferred to impregnate them with a drug-proofing substance and, optionally, a water-proofing substance, as are well known in the art.

The adhesive is generally provided as a layer, which is preferably laminated directly onto the backing, although the backing itself may be multilaminate. The adhesive is suitable to directly adhere to most backings, but it may be necessary, or desirable, in some instances, to provide further means for the adhesive to be secured to the backing, such as by a cross-linking layer.

While it is generally not preferred or necessary to incorporate other ingredients in the adhesives of the present invention, it will be appreciated extra formulants may be added as desired and that certain formulations or conditions may benefit from other ingredients. For example, the addition of vegetable oils may be used to further enhance early release, suitable examples including coconut oil and groundnut oil. Such other ingredients as softeners and tackifiers may also be included, but it is generally preferred to minimise such ingredients.

Patches of the present invention are also useful in the treatment of emesis associated with fractionated chemotherapy. Fractionated chemotherapy regimens involve administering chemotherapy on successive days at reduced daily rates, which is intended to reduce side effects and increase efficacy. Unfortunately, the side effects associated with fractionated chemotherapy still include substantial nausea and vomiting and therefore 5-$HT_3$ antagonists, including granisetron, are also utilised in these treatment regimens. Fractionated chemotherapy is usually given over a five day period (although this can vary) and the associated symptoms of nausea and vomiting are prevented by daily doses of antiemetics—in the case of granisetron this is generally 2 mg per day. Hence, the pattern of administration is similar to that for the prevention of the acute and delayed emesis associated with single dose chemotherapy. Patches to protect against the nausea and vomiting associated with fractionated chemotherapy may be suitably constructed to deliver consistently higher levels of drug than one for the treatment of single dose chemotherapy, and this is readily achieved by manipulation of the patch area and loading dose.

Patches of the invention may also be used in the treatment and prophylaxis of postoperative nausea and vomiting (PONV). It will be appreciated that, where used herein, treatment includes prophylaxis, where appropriate. PONV remains a frequent and unpleasant experience for patients undergoing surgery. On average, 20 to 30 percent of surgical subjects suffer from PONV symptoms, depending on individual subject factors, type and duration of anaesthesia and type of surgery. PONV can result in dehydration, electrolyte imbalances, prolongation of stay in the recovery room, unanticipated hospital admissions and loss of work. As with the treatment of chemotherapy induced nausea and vomiting, addition of dexamethasone to the regimen improves the efficacy of the regimen.

The usual regimens to prevent post-operative nausea and vomiting are single administrations of $5HT_3$ antagonists, immediately pre- or post surgery. Such doses may be replaced by a transdermal patch applied prior to surgery, in light of recent advances in the understanding of reductions possible in the required dose of granisetron for the prevention of post-operative nausea and vomiting. In one study, clinical data suggested granisetron was effective in the prevention of post-operative nausea and vomiting at doses as low as 0.1 mg, such doses be readily dispensable by patches of the invention.

Other indications are as indicated above, and include: pruritus, the treatment and prophylaxis of fibromyalgia and pain associated therewith, migraine, anxiety, cognitive and psychotic disorders, depression, schizophrenia, psychosis in postnatal depression, irritable bowel syndrome, alcoholism, obstructive sleep disturbed breathing, motion sickness, loss of cognitive function such as Alzheimer's, urinary incontinence, dyskinesia, systemic lupus erythematosus, drug-induced pruritus, premature ejaculation, eating disorders, obsessive compulsive disorder, gastric motility disorders (diarrhoea), chronic fatigue syndrome, dyspepsia and cocaine dependence.

The present invention is further illustrated by the following, non-limiting Examples and the accompanying Figures, wherein.

EXAMPLE 1

To examine the possibility of incorporating granisetron into adhesives that contain nucleophilic monomers, the drug was formulated into four different National Starch adhesives. As listed in Table 1, one of these adhesives contained polymers with no functionality, two contained polymers with acidic functionality and the fourth hydroxyl functionality.

TABLE 1

| Adhesive | Chemical composition | Functional groups | ~% Functional Monomer |
|---|---|---|---|
| DT 4098 | Acrylate-vinylacrylate | None | 0 |
| DT 2052 | Acrylate-vinylacrylate | COOH | 5 |
| DT 2353 | Acrylate | COOH | 5 |
| DT 2287 | Acrylate-vinylacrylate | OH | 5 |

"~% Functional Monomer" indicates the approximate level of acidic or OH containing monomer (w/w) used in preparation of the adhesive, within a 10% tolerance.

Figure 1:
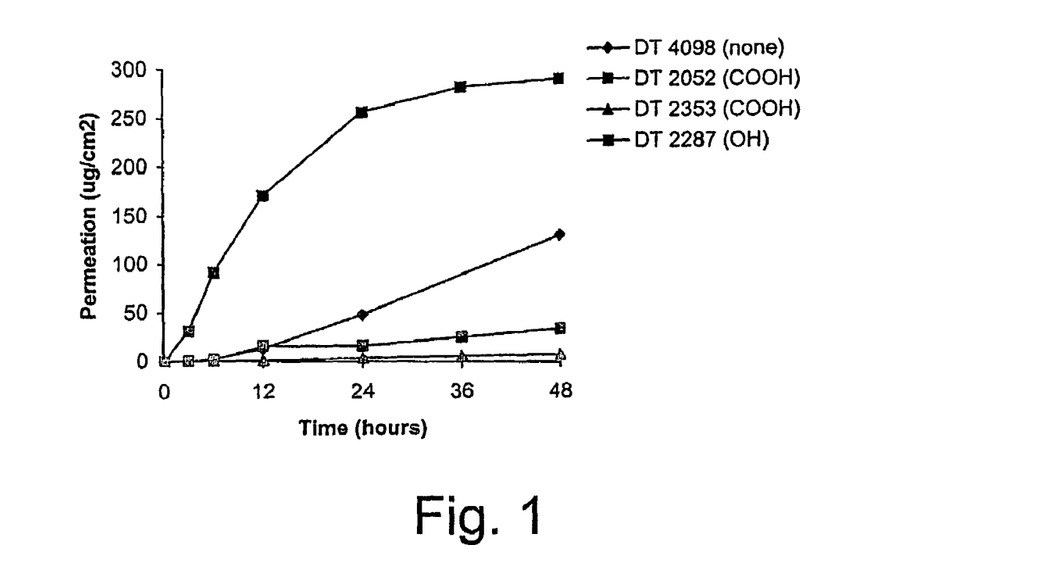
FIG. 1 depicts the in vitro murine skin permeation ($\mu g/cm^2$) of granisetron from 3% formulations of granisetron in various adhesives.

Accompanying FIG. 1 depicts the in vitro murine skin permeation ($\mu g/cm^2$) of granisetron from 3% formulations of granisetron in the adhesives listed in Table 1. Each of these formulations was produced at a coating weight of 85 $g/m^2$ to give a drug loading of approximately 260 $\mu g/cm^2$. Crystallisation was not observed in any of the devices manufactured.

Table 2 shows the levels of permeation from the various formulations at various time intervals, and shows levels of flux from DT 2287 30× greater than those obtained with the non-nucleophilic and electroneutral DT 4098. The reason for the convergence at higher levels is owing to the depletion of drug from the adhesive in DT 2287.

TABLE 2

| Adhesive | Functional groups | Permeation (µg/cm$^2$) | | | | | |
|---|---|---|---|---|---|---|---|
| | | 3 | 6 | 12 | 24 | 36 | 48 |
| DT 4098 | None | 1 | 2.9 | 13.4 | 48.5 | n/s | 129.8 |
| DT 2052 | COOH | 0.8 | 2.3 | 16.1 | 15.9 | 24.8 | 33.3 |
| DT 2353 | COOH | 0.3 | 0.8 | 1.7 | 3.7 | 5.4 | 7.2 |
| DT 2287 | OH | 31.7 | 92.0 | 170.8 | 256.6 | 282.4 | 290.4 |

Permeation from the adhesives containing acidic moieties was very much lower than that from the adhesive with no functionality.

Table 3 shows the same data as in Table 2, but treated so as to show average flux.

TABLE 3

| Adhesive | Functional groups | Average flux (µg/cm$^2$/hr) | | | | | |
|---|---|---|---|---|---|---|---|
| | | 3 | 6 | 12 | 24 | 36 | 48 |
| DT 4098 | None | 0.33 | 0.48 | 1.1 | 2.0 | — | 2.7 |
| DT 2052 | COOH | 0.27 | 0.38 | 1.3 | 0.66 | 0.69 | 0.69 |
| DT 2353 | COOH | 0.10 | 0.13 | 0.14 | 0.15 | 0.15 | 0.15 |
| DT 2287 | OH | 10.6 | 15.3 | 14.2 | 10.7 | 7.8 | 6.05 |

Table 4 shows the same data, but treated to show absolute flux, which is the taken as the gradient at the time point selected, and further highlights the superiority of the patches of the invention over the initial six hours. Patches with substantially higher loading could be expected to deliver higher doses for longer.

TABLE 4

| Adhesive | Functional groups | Absolute flux (µg/cm$^2$/hr) | | | | | |
|---|---|---|---|---|---|---|---|
| | | 3 | 6 | 12 | 24 | 36 | 48 |
| DT 4098 | None | 0.33 | 0.63 | 1.8 | 2.9 | — | 3.3 |
| DT 2052 | COOH | 0.27 | 0.50 | 2.3 | — | 0.74 | 0.71 |
| DT 2353 | COOH | 0.10 | 0.17 | 0.15 | 0.17 | 0.15 | 0.15 |
| DT 2287 | OH | 10.6 | 20.1 | 13.1 | 7.2 | 2.2 | 0.67 |

Figure 2:
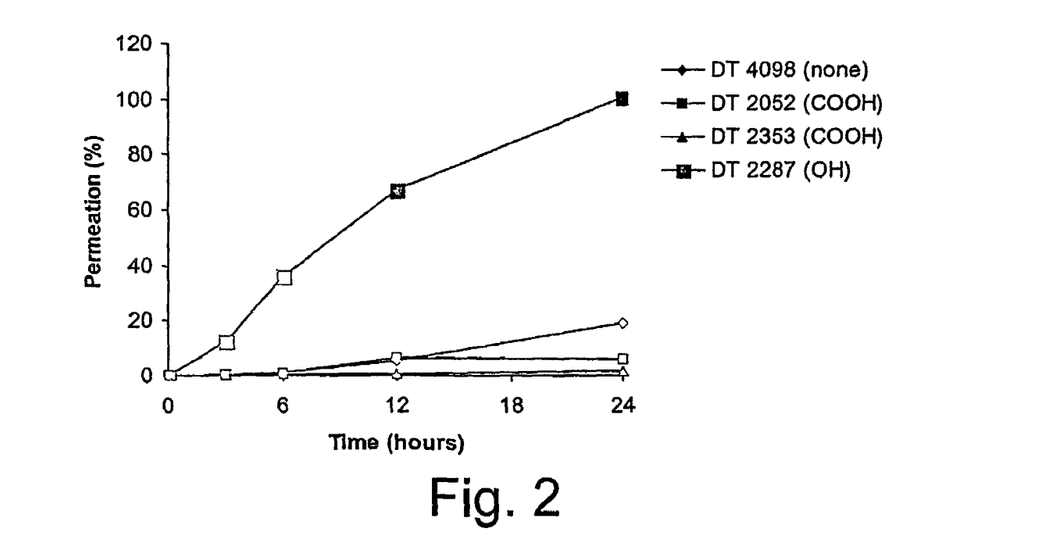
FIG. 2 shows in vitro murine skin permeation of granisetron from formulations of different adhesive polymer functionality.

A surprisingly high degree of granisetron permeation from the adhesive containing hydroxyl groups was observed (FIG. 1). The flux from this formulation was sufficiently high to deplete the device of granisetron after only 24 hours (as indicated by the plateauing of the permeation curve for the DT 2287 formulation in FIG. 1). This complete depletion indicates that it is very unlikely that any lasting interaction occurred between the drug and this adhesive. The relative depletion, in terms of %, of the formulations examined over a 24 hour period is depicted in FIG. 2, which shows in vitro murine skin permeation (% of applied dose) of granisetron from formulations of different adhesive polymer functionality, and clearly shows the surprising efficiency of the DT 2287 formulation.

EXAMPLE 2

Drug stability in the best formulation of Example 1 was investigated.

Stability data for the patches formulated in DT 2287 and stored at three temperatures for six weeks are shown in Table 5. There was no observed decrease in granisetron content of the patches indicating that, even under accelerated conditions at 40° C., the drug is stable in these devices.

TABLE 5

Stability of granisetron patches

| Storage temperature | Storage period | % Granisetron |
|---|---|---|
| 40° C. | 6 weeks | 99.3 |
| 25° C. | 6 weeks | 99.4 |
| 5° C. | 6 weeks | 99.4 |
| Standard | | 99.5 |

Figure 3:
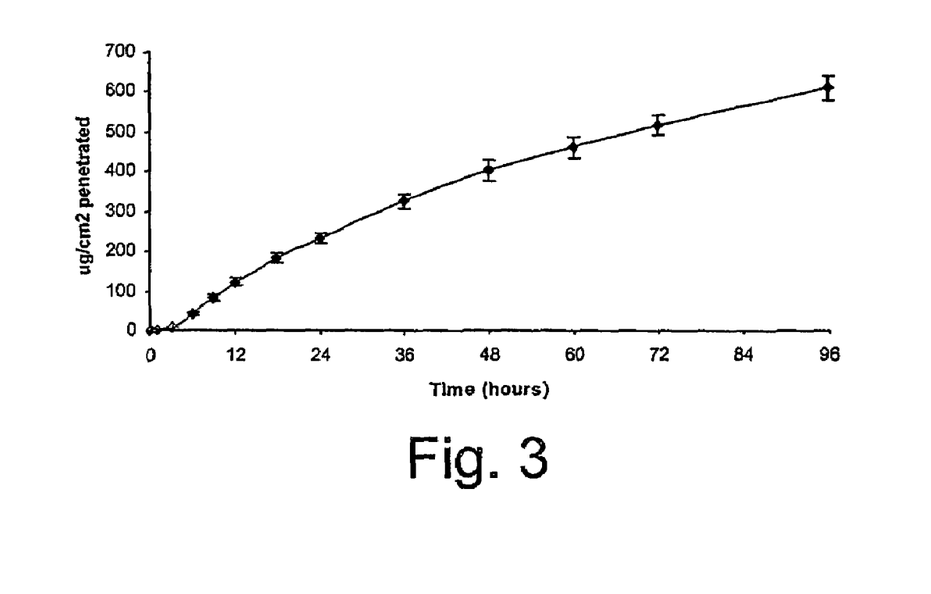
FIG. 3 shows in vitro human skin permeation of granisetron from a preferred adhesive.

FIG. 3 shows in vitro human skin permeation of granisetron from DT 387-2287 adhesive (n=4), and depicts uses an 8% granisetron formulation coated at a weight of 110 g/m$^2$. This equates to a granisetron loading of about 880 µg/cm$^2$. After 96 hours the total permeation amounted to approximately 600 µg/cm$^2$ which equates to about 70% of the patch loading. Although permeation is plateauing after 96 hours, it is assumed that the patch would continue to deliver drug for another 24 hours.

Figure 4:
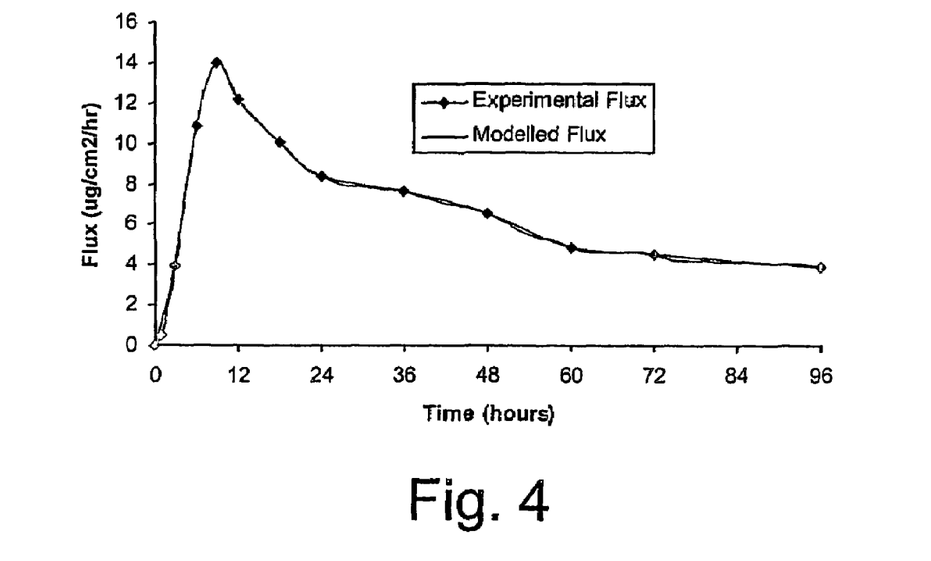
FIG. 4 shows experimental and modelled in vitro human skin permeation of granisetron from a preferred adhesive.

FIG. 4 is a plot of the gradient of FIG. 1 against time i.e. a depiction of flux against time. FIG. 4 shows experimental and modelled in vitro human skin permeation of granisetron from DT 2287 adhesive (µg/cm$^2$/hr). This flux profile was modelled and used as an input for a simple pharmacokinetic model (based on PK data from patients) to predict the in vivo performance of a 10 cm$^2$ patch as shown in FIG. 5.

Figure 5:
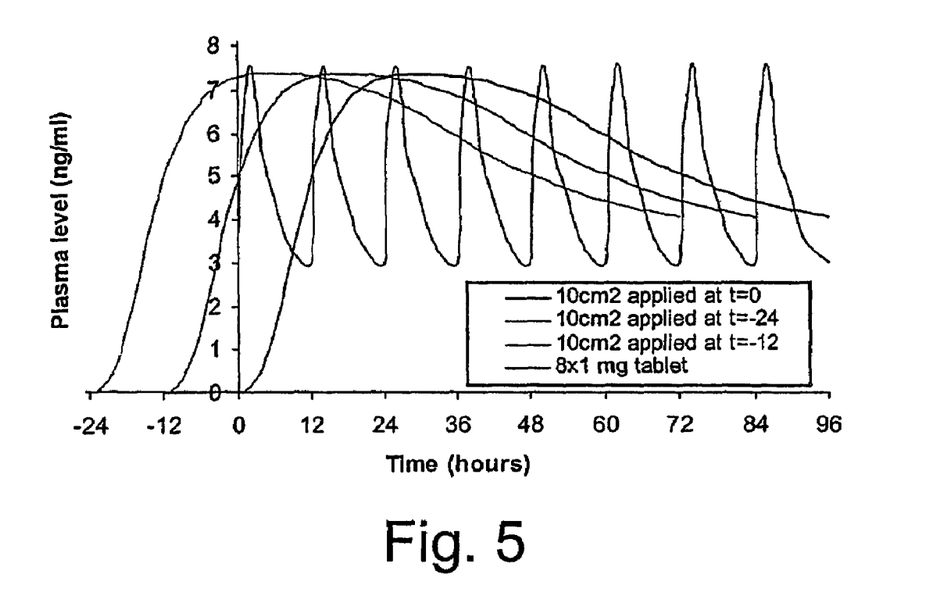
FIG. 5 shows simulated granisetron plasma profiles from a 10 $cm^2$ patch compared with experimental plasma profile at steady-state.

FIG. 5 shows simulated granisetron plasma profiles from a 10 cm$^2$ patch compared with experimental plasma profile at steady-state after repeated oral administration of 1 mg granisetron in patients.

The data in FIG. 3 are indicative that the formulation will deliver drug over several days and is suitable for a five day period, such as that over which granisetron is frequently prescribed. FIG. 3 also shows the predicted effect of applying the transdermal patch at different times i.e. prior to chemotherapy, and demonstrates how such a device may be utilised in practice to protect against acute and delayed emesis as well as emesis associated with fractionated chemotherapy.

EXAMPLE 3

Sustained Delivery of Granisetron, in vivo, in Man

Preparation of Patches

Granisetron patches were manufactured from a coating solution prepared in the following manner:
1. The solid content of DT 387-2287 was determined and the adhesive diluted with ethylacetate to the lower specification limit of 49%. The solution was then mixed by a stirrer for 15 minutes.
2. Granisetron base was dissolved in dimethylacetamide (DMA) until a clear solution (approximately 67 mg/ml) was obtained.
3. The adhesive solution obtained from 1 above was mixed with the granisetron solution obtained from 2.

The aim of the coating process was to obtain a laminate with an area weight of 110 g/sqm, a low level of residual solvents and to limit the amount of degradation of the drug during drying of the laminate.

The coating solution was coated onto the release liner (FL2000 100 µm) to achieve an area weight of 110 g/sqm. This was subsequently laminated with the backing foil Hostaphan MN 15 MED. The manufacturing and stability of the coating solution posed no problems. The active and placebo solutions were easily coated achieving the required area weight of 110 g/sqm. Good results were obtained, coating at 90° C. with a coating speed of 0.1 m/min. Patches (15 cm$^2$) were punched from the laminate and packaged in aluminium pouches. Each 15 cm$^2$ patch contained 6% w/w granisetron in adhesive (a total load of approximately 10 mg per patch or 660 μg/cm$^2$).

Figure 6:
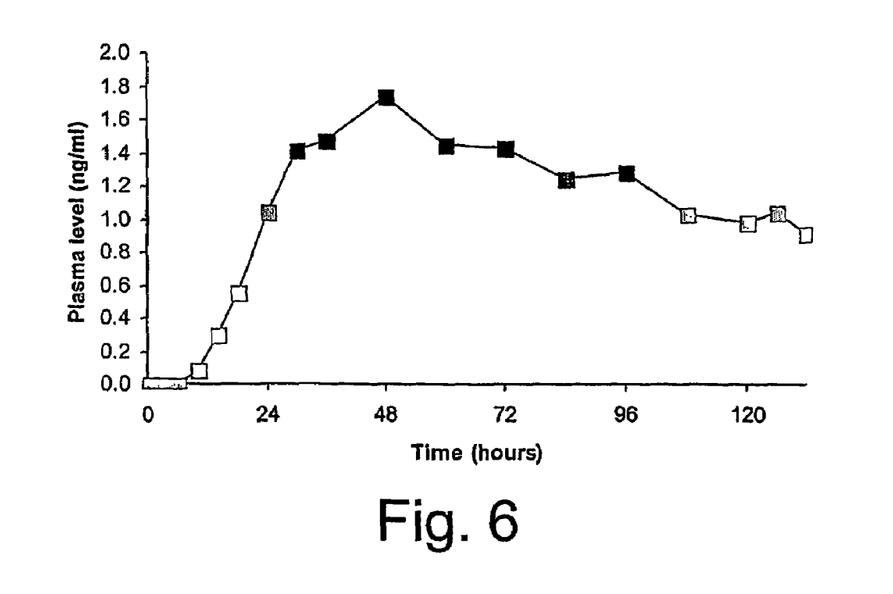
FIG. 6 shows the mean plasma level of granisetron after application of a single 15 $cm^2$ patch to human volunteers.

A phase I study in human volunteers was conducted to assess the systemic bioavailabilty of granisetron from the patch together with the local and systemic tolerance of the device. Patches were applied to the abdomens of the volunteers for a period of 5 days (120 hours) and blood samples taken during the period of application. The results are shown in Table 6 and in FIG. 6, showing the mean plasma level of granisetron after application of a single 15 cm$^2$ patch to human volunteers (n=11).

TABLE 6

| Subject | AUC$_{(0-132)}$ (h · ng/ml) | C$_{max}$ (ng/ml) |
|---|---|---|
| Mean | 148 | 1.9 |
| SD | 117 | 1.3 |
| % CV | 79 | 72 |
| Geometric mean | 114 | 1.5 |
| Geometric mean. % CV | 88 | 72 |

AUC = area under the curve from time zero to 132 hours
C$_{max}$ = maximum concentration achieved.
SD = standard deviation
% CV = percent coefficient of variation The data in FIG. 6 are the plasma levels of granisetron obtained by taking samples from the volunteers.

The study demonstrated the sustained bioavailability of granisetron via a 15 cm$^2$ transdermal patch. The patch demonstrated low dermal irritation potential and acceptable adhesiveness. The granisetron patch was safe and well tolerated in all subjects, both locally and systemically.

Taking the in vivo data from the human volunteer study using a patch of 15 cm$^2$, and taking into consideration a pharmacokinetic analysis and comparison with the known C$_{max}$ (3.6 ng/ml) in human volunteers, after a single administration of a 1 mg tablet of granisetron (Physicians Desk Reference, entry for Kytril), it was concluded that a slightly larger patch, in the region of 40 cm$^2$, would deliver appropriate levels of granisetron for optimum efficacy. A patch of this area is readily acceptable. It will be understood that the size of the patch may be determined in accordance with the patient's requirements and the experience of the practitioner, and that patches both smaller and larger than 40 cm$^2$ may be employed, as desired.

REFERENCES

Porzio G, Aielli F, Narducci F, Cannita K, Piccolo D, Marchetti P. Pruritus in a patient with advanced cancer successfully treated with continuous infusion of granisetron. Support Care Cancer. Jan. 21, 2004.
Biswas B N and Rudra A. Comparison of granisetron and granisetron plus dexamethasone for the prevention of postoperative nausea and vomiting after laparoscopic cholecystectomy. Acta Anaesthesiol. Scand. 47, 79-83 (2003).
The, GK, Prins J., Bleijenberg, G., van der Meer, J. W., Neth. J. Med., September, 2003; 61(9): 285-9.
Cupissol D, Bressolle F, Adenis L, Carmichael J, Bessell E, Allen A, Wargenau M, and Roman D. Evaluation of the bioequivalence of tablet and capsule formulations of granisetron in patients undergoing cytotoxic chemotherapy for a malignant disease. J. Pharm. Sci. 82, 1281-1284 (1993).
Friedman C J, Burris H A I, Yocom K Blackburn L M and Gruben. Oral granisetron for the prevention of acute late onset nausea and vomiting in patients treated with moderately emetogenic chemotherapy. Oncologist 5, 136-143 (2000).
Gralla R J, Osaba D, Kris M G, Kirkbride P, Hesketh P J, Chinnery L W, Clark-Snow R, Gill D P, Groshen S, Grunberg S, Koeller J M, Morrow G R, Perez E A, Silber J H, and Pfister D G. Recommendations for the use of antiemetics: evidence-based, clinical practice guidelines. J. of Clinical Oncology. 17, 2971-2994 (1999).
Guillem V, Carrato A, Rifa J. High efficacy of oral granisetron in the total control of cyclophosphamide-induced prolonged emesis. Proceedings of American Society of Oncology, 17, 46 (1998).
Haus U, Varga B, Stratz T, Spath M, Muller W. Oral treatment of fibromyalgia with tropisetron given over 28 days: influence on functional and vegetative symptoms, psychometric parameters and pain. Scand. J. Rheumatol. 113, 55-8 (2000).
Kalaycio M, Mendez Z, Pohlman B, Overmoyer B, Boparai N, Jones E, and Bolwell B. Continuous-infusion granisetron compared to ondansetron for the prevention of nausea and vomiting after high-dose chemotherapy. J. Cancer Res. Clin. Oncol. 124, 265-269 (1998).
Macciocchi A, Chernoff S B and Gallagher S C. A phase II dose-ranging study to assess single intravenous doses of palonosetron for the prevention of highly emetogenic chemotherapy-induced nausea and vomiting. Proceedings of American Society of Oncology, 21, 1480 (2002).
Noble A, Bremer K, Goedhals L, Cupissol D and Dilly S G. A double-blind, randomised, crossover comparison of granisetron and ondansetron in 5-day fractionated chemotherapy:assessment of efficacy, safety and patient preference. Eur. J. Cancer. 30, 1083-1088 (1994).
Physicians Desk Reference (2001). Entry for Kytril®.
VanDenBerg C M, Kazmi Y, Stewart J, Weidler D J, Tenjarla S N, Ward E S, Jann M W. Pharmacokinetics of three formulations of ondansetron hydrochloride in healthy volunteers: 24-mg oral tablet, rectal suppository, and i.v. infusion. Am. J. Health Syst. Pharm. 57, 1046-50 (2000)
de Wit R, Beijnen J H, van Tellingen O, Schellens J H, de Boer-Dennert M, Verweij J. Pharmacokinetic profile and clinical efficacy of a once-daily ondansetron suppository in cyclophosphamide-induced emesis: a double blind comparative study with ondansetron tablets. Br. J. Cancer 74, 323-6 (1996).

The invention claimed is:

1. An adhesive patch suitable for the transdermal administration of granisetron to a subject in need thereof, said patch comprising:
   an acrylic adhesive consisting essentially of:
      50 to 98% w/w of a primary acrylate monomer wherein said primary acrylate monomer is either 2-ethylhexyl acrylate or butyl acrylate, and
      0.5 to 20% w/w of a monomer containing non-acidic hydroxyl moieties, and
   a physiologically effective amount of granisetron loaded in the acrylic adhesive,
   wherein the granisetron content of said patch remains substantially unchanged when stored at 25° C. for six weeks.

2. A patch according to claim 1, wherein the monomer containing non-acidic hydroxyl moieties is selected from the group consisting of hydroxymethyl acrylates, hydroxyethyl acrylates and hydroxypropyl acrylates.

3. A patch according to claim 1, wherein the monomer containing non-acidic hydroxyl moieties is selected from the group consisting of hydroxymethyl methacrylates and hydroxyethyl methacrylates.

4. A patch according to claim 1, which is pressure sensitive.

5. A patch according to claim 1, containing 50 to 90% w/w of said primary acrylate monomer.

6. A patch according to claim 1, adapted to provide a pharmacologically effective amount of granisetron to said subject within about 2 hours after administration thereof.

7. A patch according to claim 1, having up to about 10% by weight of granisetron.

8. A patch according to claim 7, having less than 8% w/w granisetron.

9. A patch according to claim 1, having a level of granisetron above 4% w/w.

10. A patch according to claim 7, having a level of between 6% and 7.7% w/w of granisetron.

11. A patch according to claim 1, wherein no crystallisation is observed after one month storage at room temperature and pressure.

12. A patch according to claim 1, for the treatment and/or prophylaxis of chemically induced emesis.

13. A patch according to claim 12, wherein the emesis is acute.

14. A patch according to claim 12, wherein the emesis is delayed.

15. A patch according to claim 1, for the treatment and/or prophylaxis of emesis associated with fractionated chemotherapy.

16. A patch according to claim 1, for the treatment and/or prophylaxis of postoperative nausea and vomiting.

17. A patch according to claim 1, for the treatment and/or prophylaxis of nausea and vomiting associated with radiotherapy.

18. A patch according to claim 1, for the treatment and/or prophylaxis of nausea and vomiting associated with fractionated cancer therapy.

19. A patch according to claim 1, wherein the acrylic adhesive is loaded with between 3 and 12% w/w granisetron.

20. A patch according to claim 19, wherein the acrylic adhesive is loaded with between 4 and 10% w/w granisetron.

21. A patch according to claim 19, wherein the acrylic adhesive is loaded with between 5 and 8% w/w granisetron.

22. A patch according to claim 1, incorporating no plasticizers or permeation enhancers.

23. A patch according to claim 1, wherein, at an acrylic adhesive loading of 6% w/w of active granisetron, the acrylic adhesive has a surface area of between 10 and 100 $cm^2$.

24. A patch according to claim 23, wherein the acrylic adhesive has a surface area of between 15 and 50 $cm^2$.

25. A method for the treatment and/or prophylaxis of any form of nausea or emesis associated with $5\text{-}HT_3$ receptor activity in a patient in need thereof, said method comprising applying an adhesive patch according to claim 1 to the skin of the patient.

26. A method for the treatment and/or prophylaxis of chemotherapy induced nausea and vomiting in a patient in need thereof, said method comprising applying an adhesive patch according to claim 1 to the skin of the patient.

27. A patch according to claim 1, for the treatment and/or prophylaxis of chemotherapy-induced nausea and vomiting.

28. A patch according to claim 1, wherein the granisetron content of said patch remains substantially unchanged when stored at 40° C. for six weeks.

* * * * *

UNITED STATES PATENT AND TRADEMARK OFFICE
CERTIFICATE OF CORRECTION

| | | |
|---|---|---|
| PATENT NO. | : 7,608,282 B2 | Page 1 of 1 |
| APPLICATION NO. | : 10/544259 | |
| DATED | : October 27, 2009 | |
| INVENTOR(S) | : Peter Altenschopfer et al. | |

It is certified that error appears in the above-identified patent and that said Letters Patent is hereby corrected as shown below:

On the cover page,

Item [*] Notice: Subject to any disclaimer, the term of this patent is extended or adjusted under 35 U.S.C. 154(b) by 260 days Delete the phrase "by 260 days" and insert -- by 352 days --

Signed and Sealed this

Fifteenth Day of June, 2010

David J. Kappos
*Director of the United States Patent and Trademark Office*